(12) United States Patent
Cunnington et al.

(10) Patent No.: US 6,232,491 B1
(45) Date of Patent: May 15, 2001

(54) PURIFICATION PROCESS FOR REMOVAL OF IMPURITIES IN ACETIC ACID-ETHYLENE REACTIONS

(75) Inventors: Malcolm J. Cunnington, East Yorkshire; Mohammed Hussain Khan, Hants; Witold Franciszek Pacynko, East Yorkshire, all of (GB)

(73) Assignee: BP Chemicals Limited, London (GB)

( * ) Notice: Subject to any disclaimer, the term of this patent is extended or adjusted under 35 U.S.C. 154(b) by 0 days.

(21) Appl. No.: 09/298,999

(22) Filed: Apr. 26, 1999

(30) Foreign Application Priority Data

Apr. 25, 1998 (GB) .................................. 9808847
Jan. 7, 1999 (GB) .................................. 9900192

(51) Int. Cl.$^7$ .................................. C07C 67/48
(52) U.S. Cl. .................................. 560/248; 560/241
(58) Field of Search .................................. 560/248, 241

(56) References Cited

U.S. PATENT DOCUMENTS 2,741,632    4/1956    Cottle .
5,206,434    4/1993    Scates et al. .

FOREIGN PATENT DOCUMENTS 0 601 929 A1    6/1994    (EP) .
1438410         6/1976    (GB) .
93072899        3/1993    (JP) .
7-17907         1/1995    (JP) .
371201         10/1973    (SU) .
98/42652   *   10/1998    (WO) .

* cited by examiner

Primary Examiner—Paul J. Killos
Assistant Examiner—John N Calve
(74) Attorney, Agent, or Firm—Nixon & Vanderhye

(57) ABSTRACT

This invention is a process for the removal of acetaldehyde impurities from ethyl acetate formed by reacting acetic acid with ethylene over a catalyst by refining a crude mixture of ethyl acetate, diethyl ether, acetaldehye and water in a column (C) so as to remove (a) refined ethyl acetate as a base product to be further purified, and (b) light ends mixture comprising diethyl ether and acetaldehyde overhead to be fed to an aldehyde removal column; a purge comprising acetaldehyde is removed at or near the top of the aldehyde removal column. The process is a very important step in the commercial manufacture of ethyl acetate because the presence of acetaldehyde is detrimental to the esterification catalyst.

28 Claims, 1 Drawing Sheet

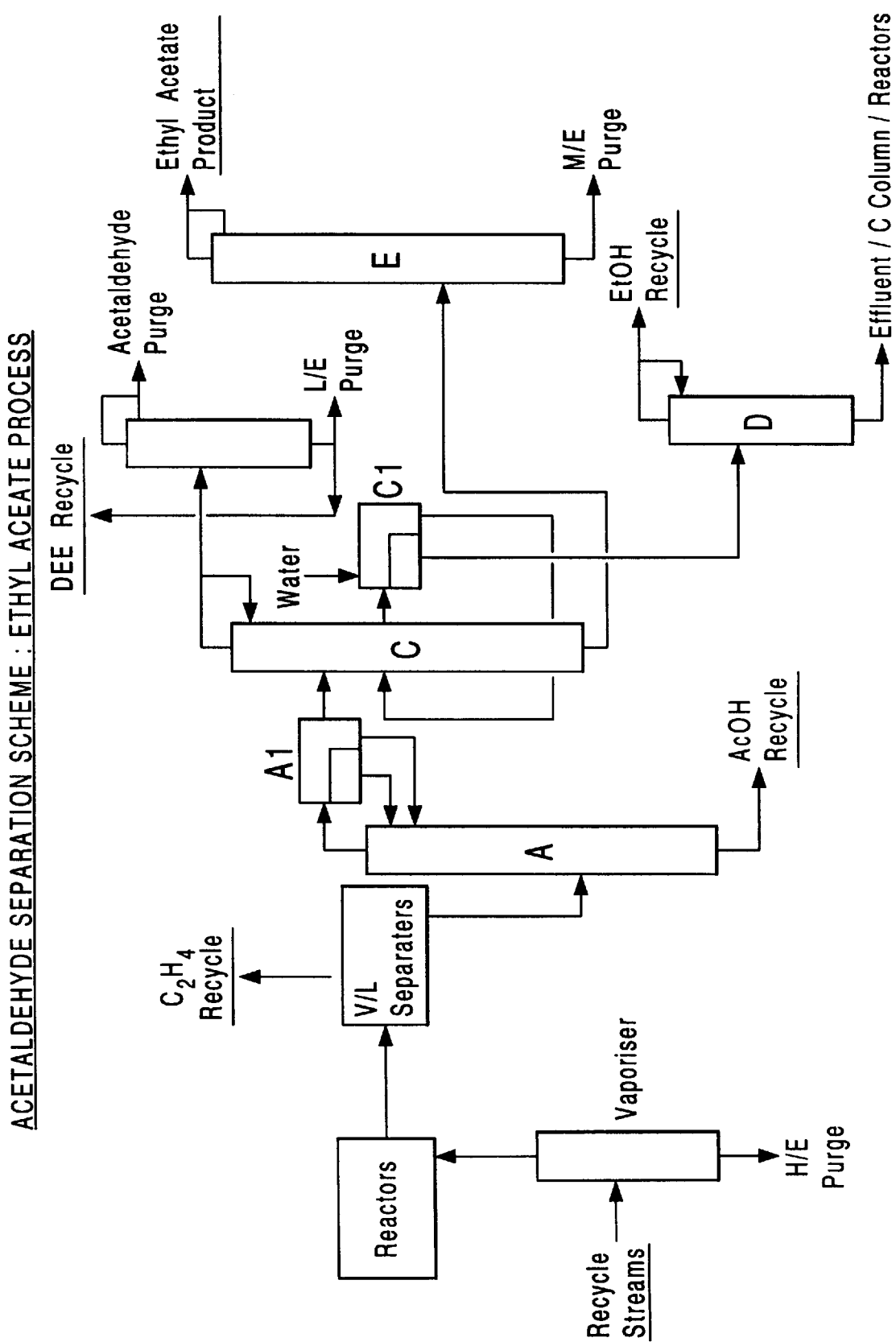

PURIFICATION PROCESS FOR REMOVAL OF IMPURITIES IN ACETIC ACID-ETHYLENE REACTIONS

BACKGROUND OF THE INVENTION AND SUMMARY OF THE INVENTION

This invention relates to a process for the production of esters by the direct addition of a saturated lower carboxylic acid to an olefin in the presence of a catalyst and to a method of purifying the recycle streams to the process to prolong catalyst activity and catalyst life.

It is well known to produce esters such as ethyl acetate or n-butyl acetate by an esterification reaction of ethanol or n-butanol respectively with acetic acid in the presence of an acidic catalyst. One such method is described in GB-A-1438410. It is also known to produce esters such as these by the addition of an acid to an olefin. The process for making ethyl acetate by the direct addition of acetic acid to ethylene produces a range of by-products and impurities. While some of the main by-products are similar to those removed from ethyl acetate made by esterification of acetic acid (eg ethanol and diethyl ether), the process is intrinsically different and therefore produces a range of quite different by-products as impurities. More specifically, because ethylene is one of the reactants there is scope for oligomerisation thereof resulting in a range of by-products including inter alia hydrocarbons ranging from ethane and butane through to longer chain hydrocarbons of 10–12 or more carbon atoms. These by-products can include both saturated and unsaturated hydrocarbons and may also contain oxygenated compounds. It is known that slowly with time during this direct addition reaction, some deactivation of catalyst is observed and one of the reasons for this was believed to be the formation of coke derived from aromatic and olefinic materials. However, to date no aromatics have so far been detected in the product streams of the direct addition reaction.

In order to minimise this catalyst deactivation, it was decided to use a product purification process involving steps of distillation and recycle during the direct addition process. The distillation scheme primarily comprises an initial column to which the liquid addition reaction products are fed (via flash separators) and from which excess/unreacted acetic acid and heavy ends are removed, a second column from which the light ends, ethanol and water are removed to generate a crude ethyl acetate product, a third column in which the alcohol (and any ethyl acetate) are separated from water in order to enable recovery of the alcohol for recycling and a fourth column in which the crude ethyl acetate from the second column is refined and purified by removal of any residual by-products passed overhead of the second column as azeotropes with eg water and the medium ends which are purged from the base of this column. However, the designs used hitherto had no provision for the removal of aldehyde by-products (which are known to cause catalyst deactivation) formed during the reaction. The reason for this is that it had always been believed that the deactivation of the catalyst was due to coking of aromatics or olefins as stated above.

It has now been found that for ethyl acetate produced in a direct addition reaction, the distillation scheme can be tailored not only to remove a new range of impurities characteristic to the direct addition process but also to ensure that the recycle streams are of a sufficient quality thereby avoiding the impairment of catalyst activity or lifetime.

Accordingly, the present invention is a process for the purification of the reaction products of a direct addition reaction comprising reacting ethylene with acetic acid in the presence of a catalyst to form ethyl acetate and purifying the recycle streams, the purification process comprising the steps of:

(i) feeding the reaction products to an acid removal column (A) where acetic acid is removed from the base of the column, at least a fraction comprising light ends comprising inter alia hydrocarbons, ethyl acetate, ethanol, diethyl ether and water are withdrawn overhead and fed into a decanter (A1) for separation of said overheads into an ethyl acetate-rich phase and an aqueous (water-rich) phase, (ii) recycling at least a portion of the ethyl acetate-rich phase and substantially all of the aqueous phase from decanter (A1) as reflux separately back to column (A) at or near the top thereof, (iii) feeding the remainder of the ethyl acetate-rich phase from decanter (A1) to a refining column (C) at or near the top thereof, (iv) removing from column (C):
  (a) a base product comprising substantially refined ethyl acetate which is fed to a purification column (E);
  (b) an overhead product comprising light ends including inter alia acetaldehyde and diethyl ether which is fed to an aldehyde removal column; and
  (c) a side-draw comprising primarily ethyl acetate, ethanol and some water which is removed at a point below the feed point of the ethyl acetate-rich phase from column (A), (v) removing a purge comprising acetaldehyde at or near the top of the aldehyde removal column and recycling the diethyl ether recovered from the base of the aldehyde removal column to the esterification reactor, and (vi) purifying the refined ethyl acetate in column (E).

The catalyst used for this addition reaction is suitably an acid catalyst and may be selected from phosphoric acid, phosphonic acid and a heteropolyacid catalyst. It is preferably a heteropolyacid catalyst which may be supported on a carrier. The carrier, where used is suitably silica which may be in any shape or form selected from beads, agglomerates, globules, pellets, extrudates and granules.

Specific examples of such silicas include, but are not limited to the Degussa 350 silica (ex Degussa) and Grace 57 grade silicas (ex W R Grace). The reaction may be carried out using commercial acetic acids and may include an amount of diethyl ether which is recovered from the reaction products and is recycled to this step.

The Table below shows a typical composition of the reaction products of a direct addition reaction which is used as feed to the acid removal column (A).

Depending on the age of the catalyst and the way the process is operated the relative concentration of the components changes Table I below gives a view that is currently observed.

TABLE 1

| Component | Concentration by weight |
|---|---|
| Ethyl acetate | 46.95 |
| Acetic acid | 38.35 |
| Water | 11.41 |
| Ethanol | 1.83 |
| Diethyl Ether (DEE) | 0.59 |
| Acetaldehyde | 0.03 |
| Light Ends | 0.91 |
| Medium Ends | 0.06 |
| Heavy Ends | 0.01 |

BRIEF DESCRIPTION OF THE FIGURE

The invention will now be described in more detail with reference to the accompanying FIGURE which is a schematic diagram of a purification section in a distillation train during the production of ethyl acetate by the direct addition process.

DETAILED DESCRIPTION OF THE INVENTION

The accompanying FIGURE below is a schematic diagram of the purification section in the distillation train during the production of ethyl acetate by the direct addition process. The distillation train suitably comprises at least 5 columns. The first column is an acid removal column (A) which separates the product stream from the reactant acetic acid and "heavy ends". At least a portion of the acid, water and heavy ends from the base of the column (A) may be removed as purge at or near the base of the column (A) and may optionally be passed through an ion (eg cation) exchange resin bed to remove dissolved/suspended corrosive metals and then the eluate therefrom may be fed to a vaporiser to generate recyclable acetic acid which in turn may be mixed with fresh acetic acid and then used to saturate ethylene reactant being fed to the reactor. At least a fraction comprising inter alia hydrocarbons, ethyl acetate, ethanol, diethyl ether and water is withdrawn overhead and fed into a decanter (A1) for separation of said overheads into an ethyl acetate-rich phase and an aqueous (water-rich) phase. The product stream emerging from column (A) is then fed to an ethyl acetate refining column (C) where a volatile stream comprising mainly diethyl ether, acetaldehyde and other Light Ends are removed overhead as distillate from the product stream. The distillate stream from the refining column (C) is then passed to an aldehyde removal column where acetaldehyde is removed by distillation from the diethyl ether as a distillate.

Most of the diethyl ether stream containing some other Light Ends emerging from the base of the aldehyde column is returned to the reactor as a recycle stream but a small portion of this stream is purged from the process. This avoids a build up of Light Ends impurities. The ethanol and water (along with some ethyl acetate) are suitably removed as a side-draw from column (C), suitably after being cooled, are passed suitably into a mixer which may be a static mixer to achieve intimate mixing and coalescence thereof and the intimate mixture fed to a decanter (C1) allowing an organic phase comprising the ethyl acetate to separate from an aqueous phase comprising ethanol, optionally after one or more steps of washing the organic phase with water to remove the ethanol along with the water washings into the aqueous phase. The separation of the two phases can be assisted by the use of decanter internals such as eg plate packing. The aqueous phase, which contains most of the ethanol, is suitably passed to a water purification column (D) from which an overhead stream rich in ethanol can be recovered, and a base stream comprising essentially water can be recovered. The organic phase contains a small concentration of aqueous phase existing as a separate phase with a concentration of the aqueous phase in the total organic phase suitably below 1000 ppm, preferably less than 300 ppm and typically from abouit 90–220, if the costs of the column (C) are kept in perspective and do not outweigh the benefits of reducing this concentration below that level. The amount of aqueous phase slippage into the ethyl acetate phase can be reduced by the controlling the residence time of the intimate mixture within the decanter and/or by using decanter internals. The organic phase recovered from the decanter (C1) is suitably returned to column (C) preferably at a point just below the point of removal of side-draw from column (C) referred to above. The crude ethyl acetate passes out of the base of column (C) and is suitably fed to an ethyl acetate polishing column (E). The function of column (E) is to separate some of the medium ends and any heavy end hydrocarbons from the crude ethyl acetate stream. This is suitably carried out using a distillation technique, whereby these impurities are allowed to concentrate and are purged from the base of column (E). The purified ethyl acetate product is removed from the heads of column (E). If further purification/treatment of the ethyl acetate emerging from column (E) is desired, it may be passed through some further optional polishing beds/columns.

Liquid leaving the low pressure flash system enters the acid removal column (A) whose function is to separate acetic acid and any heavy hydrocarbons from the product stream. This column (A) can be operated at atmospheric or elevated pressure.

For the purposes of this example we have defined the separation capabilities of the columns in terms of either actual experimental trays (with a corresponding tray efficiency) or the number of theoretical stages required for the separation. The definitions are interchangeable provided that the tray efficiency of a distillation tray to be used (or the height equivalent to a theoretical plate (HETP), if a packed column is used) are known. In this example, column (A) was operated at atmospheric pressure and had 53 trays (with an efficiency of approximately 50% giving a total of 27 theoretical stages) with the feed point located at tray 33 (from the top). The ethyl acetate product, present as either the ethanol and/or water azeotrope and all the light ends passed over the head of column (A) as a heads stream which were condensed and passed to a decanter which is suitably sub-cooled, operating at 40° C. Here the heads stream was allowed to separate into two phases, one rich in ethyl acetate and the other an aqueous (water-rich) phase. Column (A) operated at an organic reflux ratio of 0.5:1 (if internal reflux is taken into consideration, the total organic reflux ratio will be 1:1) so that half of the organic product was returned to column (A).

All of the aqueous phase was also returned as reflux. Although this also helped the separation in the column(A), the aqueous phase contained relatively high levels of acetaldehyde. If this aqueous phase was passed directly to the water purification column (D), acetaldehyde would inevitably be recycled back to the reactor with the ethanol. This must be avoided due to the detrimental effect of acetaldehyde on the catalyst. Refluxing the aqueous phase in this way ensures that all the acetaldehyde entering the system passes onto the ethyl acetate refining column (C) where it can be removed from the system.

There are two alternative ways of operating column (A). These are: with the column either (a) in an ethyl acetate-filled mode or (b) in a water-filled mode. The former mode (a) has been conventional in esterification since the water in the base of column (A) is an important control variable. It needs to be kept low which would mean that operating column (A) in the water-filled mode would not be possible. It has been found that column (A) can be operated in either mode but the water-filled mode offers a substantial advantage in that it can be run largely free of organic reflux thereby saving both capital and operating costs. The details of these two modes (operating under atmospheric pressure) are respectively shown in Tables 2–5 below:

a. Ethyl Acetate Full Mode

TABLE 2

| Component | Feed | Heads Product | Base Product |
|---|---|---|---|
| | | Amounts in % by wt | |
| Acetic Acid | 37.9 | 0.0 | 81.4 |
| Ethyl acetate | 47.0 | 87.3 | 0.03 |
| Diethyl Ether | 1.3 | 2.5 | 0 |
| Water | 11.3 | 4.9 | 18.6 |
| Ethanol | 1.8 | 3.3 | 0.2 |
| Acetaldehyde | 0.03 | 0.01 | 00 |
| Light Ends | 0.91 | 1.7 | 0 |
| Medium Ends | 0.06 | 0.11 | 0 |
| Heavy Ends | 0.01 | 0 | 0.02 |
| Total (kg/hr) | 63,279 | 33,816 | 29,463 |

Any ethylene and any lower hydrocarbons entering the system can be disengaged in column (A) and can be removed overhead. Under the above conditions the following temperature profiles shown in Table 3 below were observed.

TABLE 3

| Tray Number | Temperature (° C.) |
|---|---|
| 1 | 70 |
| 15 | 71 |
| 33 | 78 |
| 43 | 85 |
| 53 | 105 | b. Water-Filled Mode

Unlike conventional esterification processes, it is possible to operate column (A) so that the middle section of column (A) is filled with a liquid substantially comprised of water. This means that the acid is pushed down column (A) and the ethyl acetate up column (A). Column (A) can be operated with less reflux than that needed for the ethyl acetate-filled mode thereby minimising usage of steam. The composition of the streams in this mode obtained from a run with 37 theoretical stages are shown in Table 4 below:

TABLE 4

| Component | Feed | Heads Product | Base Product |
|---|---|---|---|
| | | Amounts in % by wt | |
| Acetic Acid | 37.9 | 0.0 | 81.4 |
| EtAc | 46.7 | 87.4 | 0 |
| Diethyl Ether | 1.3 | 2.5 | 0 |
| Water | 11.3 | 4.9 | 18.6 |
| Ethanol | 1.8 | 3.4 | 0 |
| Acetaldehyde | 0.03 | 0.05 | 0 |
| Light Ends | 0.91 | 1.7 | 0 |
| Medium Ends | 0.06 | 0.11 | 0 |
| Heavy Ends | 0.01 | 0 | 0.02 |
| Total (kg/hr) | 63,279 | 33,816 | 29,463 |

The temperature profile of column (A) is shown in Table 5 below:

TABLE 5

| Stage Number | Temperature (° C.) |
|---|---|
| 1 | 73 |
| 12 | 81 |
| 24 | 95 |
| 37 | 106 |

Ion Exchange Beds and Vaporiser

A ion-exchange resin bed may optionally be used to remove impurities from a liquid comprising the unreacted acid, water and heavy ends recovered from the base of column (A), the liquid being suitably fed to a coalescer to remove any oily material (heavy hydrocarbons dispersed in the unreacted acid) prior to being fed through an optional ion exchange bed capable of removing dissolved/suspended corrosive metals and generating an eluate comprising acetic acid and water. The ion exchange resin used in the bed is suitably a cationic exchange resin such as Purolite® CT145 (ex Purolite) or Anberlyst® A16 (ex Rohm & Haas). These resins are relatively stable at the temperature encountered in the base of column (A). The liquid is fed to these resin beds to remove any metals which may dissolve in the reactant acid by corrosion as the acid passes through column (A). Such metals generated by corrosion are known to be catalyst poisons and this step protects the reactor and the catalyst from any entrained metals passing over the head of the vaporiser, thereby reducing the risk of depositing heavy metals on the catalyst.

The liquid exiting the resin beds (ie the eluate) is then passed to tray 2 (from the top) of a vaporiser comprising 5 trays (tray efficiency about 50%) and ethylene reactant is fed to the bottom of the same vaporiser, whereby the acid, and any recycle streams fed thereto are vaporised. The vaporiser suitably contains a liquid demister at or above the top tray to minimise any liquid carry over. Fresh acetic acid is suitably fed above the top tray of the vaporiser to scrub the vapours of recycled acid as it rises up the vaporiser thereby preventing any heavy metal carry over along with the vaporised acid and ethylene. In this way the need for resin beds can be reduced.

The vaporiser also performs the task of separating any Heavy Ends present in the recycled acid. These concentrate in the base of the vaporiser along with some of the acid and can be purged from the system at a rate of about 83 kg/hr.

Ethylene saturated with vaporised acid (and any water) emerging from the vaporiser may be suitably further heated before being fed to the direct addition reactor.

The direct addition reactor train suitably consists of four fixed-bed adiabatic reactors which are preferably arranged in a radial flow configuration. The exotherm will depend upon the catalyst loading in each bed but is generally in the range from 5–15° C., eg about 8–8.5 across each catalyst bed. The reaction takes place in the vapour phase and the inlet temperature to the or each reactor is suitably about 175° C. although this may be varied depending upon the condition of the catalyst.

An acid stream is injected to the exit gases of the first three reactors to maintain the ethylene to acid ratio at the entry point to each of the reactors within a pre-determined range. Water may be added to these reactors to maintain control of the temperature of the gases fed to the next subsequent reactors in the system within a pre-determined range.

To recover as much heat as is practical, the exit gases leaving the reactor train is interchanged with the gas stream from the vaporiser referred to above, then used as a source of reboil energy on the ethyl acetate polishing column (E) referred to below, and finally to preheat the gases entering the vaporiser. The cooled reactor exist gases are further cooled to condense the liquids before they enter a liquid/gas separation system which is suitably a high pressure vapour/liquid separator (hereafter "HPVLS") which is operated under elevated pressure eg about 1100 KPa (10 barg). This enables vapours of any unreacted ethylene to be flashed off overhead and recylced back to the process loop. During the recycle, ethylene recycled back to the vaporiser by using a compressor and a purge is taken from this recycle stream to prevent build-up of inerts such as eg ethane, butane, nitrogen and carbon monoxide in the recycle loop. The reason for cooling the feed to the HPVLS is primarily to separate the bulk acid and ethyl acetate products from the non-condensable feeds and by-products. The reason for cooling these products to as low a temperature as is possible is to minimise any acetaldehyde being carried overhead and to maximise acetaldehyde removal. The HPVLS could itself be chilled thereby ensuring that any acetaldehyde in the HPVLS is entrapped in the liquid stream withdrawn from the base of this HPVLS. The liquid stream remaining in the HPVLS is passed on to a low pressure vapour/liquid separator (hereafter "LPVLS") which is operated at about 200 KPa (1 barg) and at about 40° C. Any gases in this stream are thus removed overhead and this overhead gaseous stream may be scrubbed to further ensure the removal of any acetaldehyde therein. The liquid from the LPVLS is pumped into an acetic acid recovery column (A) where the acetic acid, heavies and most of the water is separated from ethyl acetate, ethanol and any remaining reactor products. The acetic acid is recovered from the base of this column (A), which is suitably operated at about 138° C. and a pressure of about 320 KPa (2.2 barg), along with any heavy impurities and the stream is recycled back to the acid vaporiser. The liquid overhead stream from this acid recovery column (A) is in two phases (aqueous and organic) and a decanter may be used to separate the two phases. The aqueous phase may be returned to the column (A) as reflux, and is eventually removed from the base of the column along with the acid. The organic phase may be partly returned as reflux to the column (A) but is primarily recovered as the heads product of the column and is pumped into the ethyl acetate refining column (C) referred to below. The distillate stream from the ethyl acetate refining column (C) is fed to an acetaldehyde removal column as described below.

Ethyl Acetate Refining Column (C)

The ethyl acetate-rich phase from decanter (A1) containing all the Light Ends impurities including inter alia acetaldehyde and diethyl ether were fed to stage 12 (from the top) of an ethyl acetate refining column (C) containing 48 theoretical stages operating at 250 KPa (1.5 barg) and at a molar reflux ratio of 27.4:1. The primary function of this column was to remove ethanol, water and the Light Ends impurities from the product stream. The ethanol and water together with some ethyl acetate were removed as a side-draw from this column at stage 20. The ethanol was then subsequently washed from this stream using water introduced into a static mixer upstream of the decanter at the rate of 9500 kg/hr (so as to provide a ratio of rate of flow of organic to aqueous phase (in kg/hr of about 8.5–9.5:1) and the allowed to decant at 40° C. The ethyl acetate phase was returned to the column just below the side-draw location. The aqueous phase containing ethanol was pumped into column (D).

The feed point to column (C) was well above the side-draw location to avoid any of the Light Ends and particularly acetaldehyde entering the wash decanter, since organics entering this stream would have a tendency to ultimately return back to the reactor via column (D). The Light Ends components would thus accumulate in the top section of column (C) and were removed as a heads stream. Any ethylene and lower hydrocarbons remaining in the feed to this column are again allowed to disengage in column (C) and are returned overhead to the reactor via the vapour/liquid separator such that any acetaldehyde in this stream is allowed to condense and re-enter the distillation section. Typical compositions of the various streams from column (C) are shown in Table 6 below:

TABLE 6

| Component | Feed | Decanter Oil Phase | Decanter Water Phase | Heads Distillate Stream | Base Product Stream |
|---|---|---|---|---|---|
| | | Amounts in % by wt | | | |
| Acetic Acid | 0.0 | 0 | 0 | 0 | 0 |
| Ethyl acetate | 87.4 | 88.1 | 9.3 | 9.89 | 99.87 |
| Diethyl Ether | 2.5 | 0 | 0 | 61.16 | 0 |
| Water | 4.9 | 6.0 | 82.4 | 3.6 | 0 |
| Ethanol | 3.3 | 5.85 | 8.3 | 1.5 | 0 |
| Acetaldehyde | 0.05 | 0 | 0 | 0.8 | 0 |
| Light Ends | 1.7 | 0 | 0 | 23.1 | 0 |
| Medium Ends | 0.1 | 0.06 | 0 | 0 | 0.13 |
| Heavy Ends | 0 | 0 | 0 | 0 | 0 |
| Total (kg/hr) | 33,816 | 80,346 | 13,528 | 526 | 28,239 |

The temperature profile for column (C) is shown in Table 7 below:

TABLE 7

| Stage Number | Temperature |
|---|---|
| 1 | 71 |
| 5 | 95 |
| 15 | 100 |
| 25 | 104 |
| 37 | 111 |
| 48 | 111 |

When the reactor is operating in such a way as to produce low concentrations of the Medium End impurities it is possible to by-pass column (E) and save the steam usage associated with operating the ethyl acetate polishing column (E). Under these circumstances it is possible to remove the ethyl acetate product as a side draw close to the bottom of the column. In this case the less volatile heavy hydrocarbons are purged from the base of column (C) rather than treated in the E column. In this embodiment, column (C) base stream becomes the product stream.

Acetaldehyde Removal Column

A heads stream from column (C) was passed onto stage 4 (from the top) of a small acetaldehyde removal column containing 10 theoretical stages. The volatile nature of the components present in this stream necessitated the operation of this acetaldehyde removal column at elevated pressure of at least 400 KPa (at least 3 barg) and at a molar reflux ratio of 26 : 1. The column may be operated within a range of pressures up to 600 KPa (5 barg) to allow more effective removal of any inerts if still present. The acetaldehyde removal column thus had 10 theoretical stages and under these conditions allowed 98% by weight of the acetaldehyde to be purged from the system as a heads stream from this acetaldehyde removal column which stream also contained a small amount of diethyl ether. The ether loss was estimated to be 9% by weight in this stream. The base stream from the acetaldehyde removal column contained 60% by weight of diethyl ether and the remaining Light Ends impurities.

The composition of the streams from this acetaldehyde removal column operated at 600 KPa (5 barg) was as shown in Table 8 below:

TABLE 8

| Component | Feed | Heads Product | Base Product |
|---|---|---|---|
| | Amounts in % by wt unless otherwise specified | | |
| Acetic Acid | 0.0 | 0.0 | 0.0 |
| Ethyl acetate | 9.9 | 0 | 10.7 |
| Diethyl Ether | 61.2 | 81.6 | 60.2 |
| Water | 3.6 | 4.8 | 3.6 |
| Ethanol | 1.5 | 0.04 | 1.6 |
| Acetaldehyde | 0.77 | 10.2 | 0.02 |
| Light Ends | 23.1 | 4.2 | 23.9 |
| Medium Ends | 0 | 0 | 0 |
| Heavy Ends | 0 | 0 | 0 |
| Total (kg/hr) | 526 | 30.5 | 487 |

The temperature profile of this acetaldehyde removal column is shown in Table 9 below:

TABLE 9

| Stage Number | Temperature (° C.) |
|---|---|
| 1 | 87 |
| 5 | 97.0 |
| 7 | 97.5 |
| 10 | 100 |

In order to avoid a build up of some of the Light Ends such as the methyl pentanes, a purge of 70.5 kg/hr was taken from the base stream before it was returned back to the reactor.

Water Purification Column (D)

The water phase from column (C) decanter was pumped into the water purification column (D). This column (D) has 15 theoretical stages and the feed enters above stage 5 (from the top). Column (D) was operated at a reflux ratio of 0.75:1.

Column (D) removed ethanol and ethyl acetate from the water as azeotropes in the head stream and were then returned back to the reactor (as the ethanol recycle). The base stream—which was essentially water containing less than 150 ppm total organics—was then recycled back to the decanter associated with column (C), or was passed to the effluent system. Column (D) was operated at atmospheric pressure.

The composition of the stream was as shown in Table 10 below:

TABLE 10

| Component | Feed | Base | Heads |
|---|---|---|---|
| | Amounts in % by wt | | |
| Acetic Acid | 0 | 0 | 0 |
| Ethyl acetate | 9.32 | 0 | 4.33 |
| Diethyl Ether | 0 | 0 | 0 |
| Water | 82.4 | 99.99 | 12.27 |
| Ethanol | 8.31 | 0.01 | 41.36 |
| Acetaldehyde | 0 | 0 | 0 |
| Light Ends | 0 | 0 | 0 |
| Medium Ends | 0 | 0 | 0.01 |
| Heavy Ends | 0 | 0 | 0 |
| Total (kg/hr) | 13,528 | 10,807 | 2721 |

The temperature profile for column (D) is shown in Table 11 below:

TABLE 11

| Stage Number | Temperature (° C.) |
|---|---|
| 1 | 79 |
| 5 | 91 |
| 10 | 106 |
| 15 | 111 |

Ethyl Acetate Purification Column (E)

Crude ethyl acetate leaving the base of column (C) was fed to the ethyl acetate purification column (E) at tray 30 (from the top) of a 50-tray (tray efficiency assumed to be close to 67%). Column (E) was operated at a mass reflux ratio of about 2:1 so that about 50% of the distillate was returned as reflux. The column could also be operated at lower reflux ratio's if the impurities present were less than typical in the feed currently used. The ethyl propionate, medium end hydrocarbons and any heavy hydrocarbons that had passed over the head of column (A) eg as azeotropes with water were purged from the base of column (E). Column (E) was operated so that the overall ethyl acetate slippage was 0.3% of the feed to column (E).

The heavy hydrocarbons which consisted primarily of C10 hydrocarbons with some C9's were separated from the ethyl acetate relatively easily. However, the C8 hydrocarbons described above appeared to interact with ethyl acetate such that their volatility was greater than expected from their boiling points. A high reflux ratio and a relatively large column were employed to bring the concentration of these components down to acceptable levels. Olefins are undesirable in the product since, even at low concentrations, they adversely affect the odour of ethyl acetate. At this high reflux ratio a large proportion of these undesirable components were removed from the base of column (E) rather than from the heads. The composition of the various streams is shown in Table 12 below:

TABLE 12

| Component | Feed | Heads | Base |
|---|---|---|---|
| | Amounts in % by wt | | |
| Acetic Acid | 0 | 0 | 0 |
| Ethyl acetate | 99.87 | 99.99 | 69.95 |
| Diethyl Ether | 0 | 0 | 0 |
| Water | 0 | 0 | 0 |
| Ethanol | 0 | 0 | 0 |
| Acetaldehyde | 0 | 0 | 0 |
| Light Ends | 0 | 0 | 0 |
| Medium Ends | 0.13 | 0 | 30.02 |
| Heavy Ends | 0 | 0 | 0 |
| Total (kg/hr) | 28,244 | 28,120 | 124 |

Column (E) can be operated at atmospheric or elevated temperatures. At atmospheric pressures with the feed shown above the temperature profile of column (E) was shown in Table 13 below:

TABLE 13

| Tray Number | Temperature (° C.) |
|---|---|
| 1 | 77 |
| 20 | 78 |
| 40 | 79.5 |
| 50 | 82 |

Column (E) is important since it polishes the product to ensure that the concentration of impurities such as the C8 hydrocarbons are below the levels that are acceptable to customers.

Alternative Options

A number of alternative options are available for operating the distillation section in order to minimise utilities usage. In particular this is linked with the operation of the polishing column (E) when the impurities produced in the reactor are low. Under these circumstances the separation required by the polishing column is relatively less. The following alternative options are available:

a. Reduction of the reflux ratio. Provided that there is sufficient turndown capacity, column (E) can be operated at a range of reflux ratio's to suit an impurities make at any given time.
b. Switch off column (E) and operate a side-draw from column (A). This expedient enables the Medium Ends impurities to be removed (because they are slightly less volatile than ethyl acetate) as a side-draw close to the top of column (A). This may not be desirable at high impurity levels since the purge rate required is high and consequently ethyl acetate losses can be high.
c. Switch off column (E) and remove product as a side-draw from column (C). Again at low impurity levels it is possible to obtain a product of acceptable quality by removing the ethyl acetate product stream as a side-draw from a location close to the base of the column. In this instance the heavier impurities are purged from the base of column (C).
d. Switch off column (E) (or reduce reflux ratio) and pass product stream through a polishing bed. The polishing bed may comprise either activated carbon, molecular sieve, diatomaceous earth or various macro-reticular resins of either hydrophobic or hydrophilic nature. Polishing beds comprising highly porous materials may be capable of trapping the impurities.

We claim:

1. A process for the purification of the reaction products of a direct addition reaction comprising reacting ethylene with acetic acid in the presence of a catalyst to form ethyl acetate and purifying the recycle streams, the purification process comprising the steps of
   (i) feeding the reaction products to an acid removal column (A) where acetic acid is removed from the base of the column, at least a fraction comprising light ends comprising hydrocarbons, ethyl acetate, ethanol, diethyl ether and water are withdrawn overhead and fed into a decanter (A1) for separation of said overheads into an ethyl acetate-rich phase and an aqueous phase,
   (ii) recycling at least a portion of the ethyl acetate-rich phase and substantially all of the aqueous phase from decanter (A1) as reflux separately back to column (A) at or near the top thereof,
   (iii) feeding the remainder of the ethyl acetate-rich phase from decanter (A1) to a refining column (C) at or near the top thereof,
   (iv) removing from column (C):
      (a) a base product comprising substantially refined ethyl acetate which is fed to a purification column (E);
      (b) an overhead product comprising light ends including acetaldehyde and diethyl ether which is fed to an aldehyde removal column; and
      (c) a side-draw comprising primarily ethyl acetate, ethanol and some water which is removed at a point below the feed point of the ethyl acetate-rich phase from column (A),
   (v) removing a purge comprising acetaldehyde at or near the top of the aldehyde removal column and recycling the diethyl ether recovered from the base of the aldehyde removal column to the esterification reactor, and
   (vi) purifying the refined ethyl acetate in column (E).

2. A process according to claim 1 wherein the catalyst used for the addition reaction is an acid catalyst and is selected from the group consisting of phosphoric acid, phosphonic acid and a heteropolyacid catalyst.

3. A process according to claim 1 wherein the catalyst is supported on a carrier.

4. A process according to claim 1 wherein column (A) is operated at an organic reflux ratio of 0.5:1 by returning at least a portion of the organic phase and all of the aqueous phase to the column as reflux.

5. A process according to claim 1 wherein column (A) is operated either (a) in an ethyl acetate-filled mode or (b) in a water-filled mode.

6. A process according to claim 1 wherein the distillate stream from the ethyl acetate refining column (C) is fed to an acetaldehyde removal column.

7. A process according to claim 1 wherein the ethyl acetate-rich phase from decanter (A1) containing all the Light Ends impurities including acetaldehyde and diethyl ether are fed to stage 12 (from the top) of an ethyl acetate refining column (C) comprising 48 theoretical stages operating at 250 KPa and at a molar reflux ratio of 27.4:1 and wherein ethanol and water were removed as a side-draw from this column (C) at stage 20.

8. A process according to claim 1 wherein the compositions of the various streams from column (C) are as shown in Table 6 below:

TABLE 6

| Component | Feed | Decanter Oil Phase | Decanter Water Phase | Heads Distillate Stream | Base Product Stream |
|---|---|---|---|---|---|
| | | Amounts in % by wt | | | |
| Acetic Acid | 0 | 0 | 0 | 0 | 0 |
| Ethyl acetate | 87.3 | 88.1 | 9.3 | 9.89 | 99.87 |
| Diethyl Ether | 2.5 | 0 | 0 | 61.16 | 0 |
| Water | 4.9 | 6.0 | 82.4 | 3.6 | 0 |
| Ethanol | 3.3 | 5.85 | 8.3 | 1.5 | 0 |
| Acetaldehyde | 0.05 | 0 | 0 | 0.8 | 0 |
| Light Ends | 1.7 | 0 | 0 | 22.15 | 0 |
| Medium Ends | 0.1 | 0.06 | 0 | 0 | 0.13 |
| Heavy Ends | 0 | 0 | 0 | 0 | 0 |
| Total (kg/hr) | 33,816 | 80,346 | 13,528 | 526 | 28,239 |

9. A process according to claim 1 wherein the heads stream from column (C) are passed onto stage 4 from the top of an acetaldehyde removal column containing 10 theoretical stages and is operated at a pressure of of at least 400 KPa and at a molar reflux ratio of 26:1.

10. A process according to claim 9 wherein the composition of the streams from this acetaldehyde removal column is as shown in Table 8 below:

TABLE 8

| Component | Feed | Heads Product | Base Product |
|---|---|---|---|
| | Amounts in % by wt | | |
| Acetic Acid | 0 | 0 | 0 |
| Ethyl acetate | 9.9 | 0 | 10.7 |

TABLE 8-continued

| Component | Feed | Heads Product | Base Product |
|---|---|---|---|
| | | Amounts in % by wt | |
| Diethyl Ether | 61.2 | 81.6 | 60.2 |
| Water | 3.6 | 4.8 | 3.6 |
| Ethanol | 1.5 | 0.04 | 1.6 |
| Acetaldehyde | 0.77 | 10.2 | 0.02 |
| Light Ends | 23.1 | 4.2 | 23.9 |
| Medium Ends | 0 | 0 | 0 |
| Heavy Ends | 0 | 0 | 0 |
| Total (kg/hr) | 526 | 30.5 | 487 |

11. A process according to claim 9 wherein the temperature profile of the acetaldehyde removal column is as shown in Table 9 below:

TABLE 9

| Stage Number | Temperature (° C.) |
|---|---|
| 1 | 87 |
| 5 | 97.0 |
| 7 | 97.5 |
| 10 | 100 |

12. A process according to claim 1 wherein crude ethyl acetate leaving the base of column (C) is fed to an ethyl acetate polishing column (E) operated at a mass reflux ratio of about 2:1 so that about 50% of the distillate was returned as reflux.

13. A process according to claim 1 wherein the acid removal column (A) separates the light ends comprising ethyl acetate from a liquid comprising unreacted acid, water and heavy ends by removing at least a portion of the liquid as a purge at or near the base of said column (A).

14. A process according to claim 13 wherein the liquid removed from the base of column (A) is optionally fed to a coalescer to remove any oil materials comprising heavy hydrocarbons dispersed in the acid prior to being fed through an ion-exchange resin bed capable of removing dissolved and/or suspended corrosive metals and generating an eluate comprising acetic acid and water.

15. A process according to claim 13 wherein the ion-exchange resin bed is a cation exchange resin bed.

16. A process according to claim 13 wherein the liquid eluate exiting the resin beds is then passed to tray 2 from the top of a vaporiser comprising 5 trays, and ethylene reactant to the bottom of the same vaporiser, whereby the acid, and the returning recycle streams are vaporised.

17. A process according to claim 16 wherein the vaporiser is provided with a liquid demister at or above the top tray to minimise any liquid carry over.

18. A process according to claim 16 wherein fresh acetic acid is fed above the top tray of the vaporiser to scrub the vapours of recycled acid as it rises up the vaporiser thereby preventing any heavy metal carry over along with the vaporised acid and ethylene.

19. A process according to claim 17 wherein ethylene saturated with vaporised acid and any water emerging from the vaporiser is further heated before being fed to the direct addition reactor.

20. In a process for the separation of ethyl acetate from a mixture comprising as components ethanol, water and ethyl acetate, the improvement comprises:

a. intimately mixing said components to achieve coalescence thereof; and b. feeding the intimate mixture from (a) into a decanter designed to achieve separation of the ethyl acetate in an organic phase from ethanol and water in an aqueous phase such that the concentration of the aqueous phase in the organic phase is in less than 1000 ppm based on the total organic phase.

21. A process according to claim 20 wherein the concentration of the aqueous phase in the organic phase is less than 300 ppm based on the total organic phase.

22. A process according to claim 20 wherein the separation of the aqueous phase from the organic phase is achieved using a decanter which is internally designed to achieve the desired separation.

23. A process according to claim 20 wherein the internal design of the decanter comprises plate packing to achieve the desired separation.

24. A process according to claim 20 wherein the separation of the aqueous phase from the organic phase is achieved by controlling the residence time of the intimate mixture in said decanter.

25. A process according to claim 20 wherein the separation of the aqueous phase from the organic phase is achieved by using a combination of the internal design of the decanter and the residence time of the intimate mixture therein.

26. A process according to claim 4, wherein if internal reflux is taken into consideration, the total organic reflux ratio is 1:1.

27. A process according to claim 1, wherein in step (i), the aqueous phase is a water-rich phase.

28. A process according to claim 16, wherein said vaporizer comprising five trays has a tray efficiency of about 50%.

* * * * *